United States Patent [19]

Wlodarczyk et al.

[11] Patent Number: 5,280,786
[45] Date of Patent: Jan. 25, 1994

[54] FIBEROPTIC BLOOD PRESSURE AND OXYGENATION SENSOR

[75] Inventors: Marek T. Wlodarczyk, Birmingham; Charles D. Anderson; Daniel L. Vokovich, both of Ann Arbor, all of Mich.

[73] Assignee: FiberOptic Sensor Technologies, Inc., Ann Arbor, Mich.

[21] Appl. No.: 823,143

[22] Filed: Jan. 21, 1992

[51] Int. Cl.⁵ .................. A61B 5/14; A61B 5/0215
[52] U.S. Cl. ..................... 128/634; 128/670; 128/673; 128/675; 356/41
[58] Field of Search ............. 128/633, 634, 748, 670, 128/675, 673; 356/41

[56] References Cited

U.S. PATENT DOCUMENTS

| Re. 31,873 | 4/1985 | Howes . | |
|---|---|---|---|
| 3,814,081 | 6/1974 | Mori . | |
| 3,847,483 | 11/1974 | Shaw et al. . | |
| 3,866,599 | 2/1975 | Johnson . | |
| 4,114,604 | 9/1978 | Shaw et al. . | |
| 4,416,285 | 11/1983 | Shaw et al. . | |
| 4,600,015 | 7/1986 | Evans et al. . | |
| 4,623,248 | 11/1986 | Sperinde . | |
| 4,684,245 | 8/1987 | Goldring . | |
| 4,690,492 | 9/1987 | Beard . | |
| 4,727,730 | 3/1988 | Boiarski et al. . | |
| 4,730,622 | 3/1988 | Cohen . | |
| 4,776,340 | 10/1988 | Moran et al. . | |
| 4,803,992 | 2/1989 | Lemelson | 128/634 |
| 4,854,321 | 8/1989 | Boiarski | 128/634 |
| 4,934,369 | 6/1990 | Maxwell . | |
| 5,005,576 | 4/1991 | Gunther . | |
| 5,012,809 | 5/1991 | Shulze . | |
| 5,020,537 | 6/1991 | Gunther . | |
| 5,046,497 | 9/1991 | Millar | 128/637 |
| 5,048,524 | 9/1991 | Bailey . | |
| 5,058,587 | 10/1991 | Kohno et al. . | |

Primary Examiner—Lee S. Cohen
Assistant Examiner—Kevin Pontius
Attorney, Agent, or Firm—Harness, Dickey & Pierce

[57] ABSTRACT

A fiberoptic based sensor for patient care use. The sensor includes a catheter placed transcutaneously into a blood vessel which is connected to an external measuring head. A sensing tip of the catheter includes a pressure sensing element and an oxygen saturation measuring element. Features of the invention include novel tip designs, measuring head features, and approaches for enhancing measurement though correlation of the saturation and pressure readings.

19 Claims, 4 Drawing Sheets

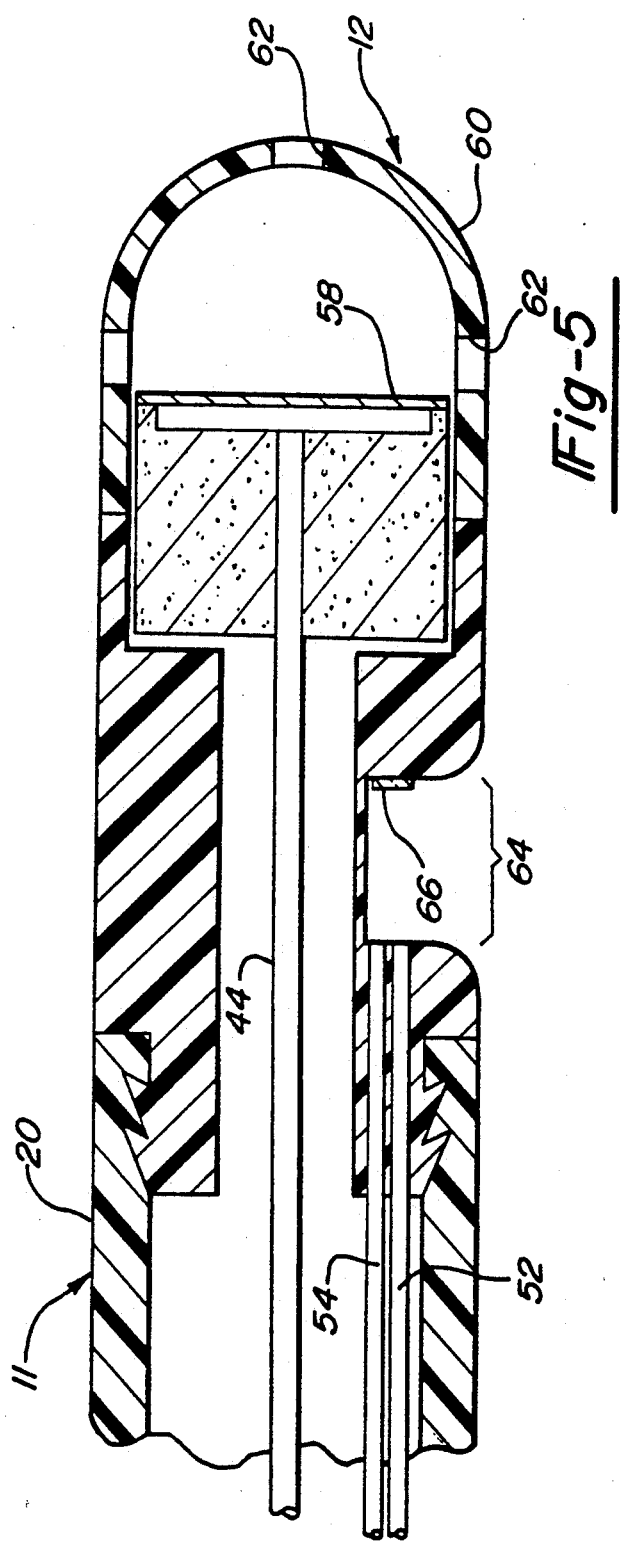
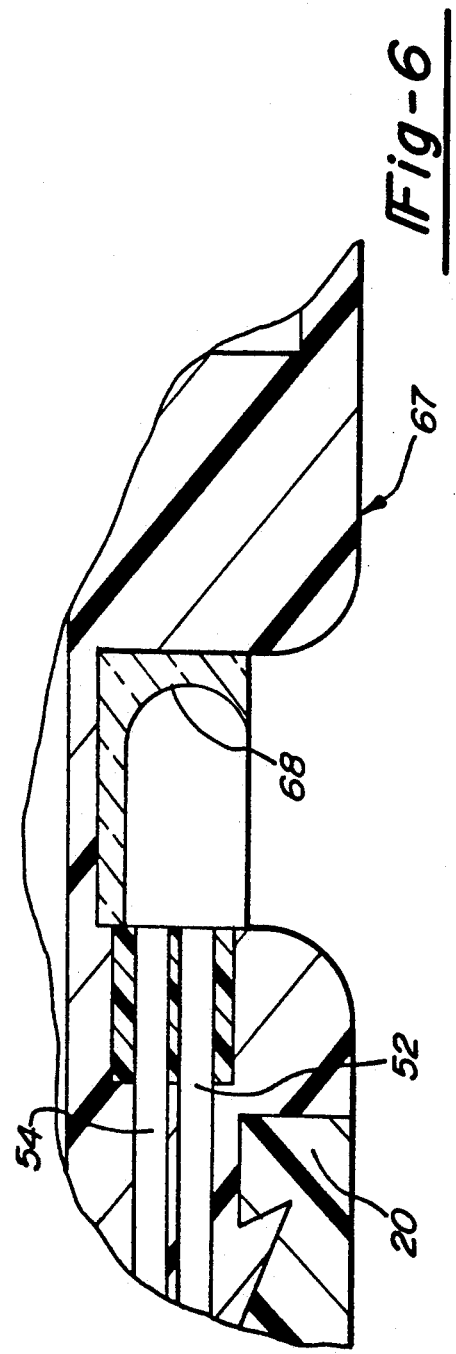
Fig-5
Fig-6

FIBEROPTIC BLOOD PRESSURE AND OXYGENATION SENSOR

BACKGROUND AND SUMMARY OF THE INVENTION

This invention is related to a system for patient care and particularly to a sensor incorporating a catheter which can be inserted transcutaneously within a blood vessel for measuring blood pressure and oxygen saturation.

In a variety of critical care situations it is desirable to continuously monitor blood pressure and oxygen saturation at remote sites within the body, for example in cardiac arteries. The present applicant, FiberOptic Sensor Technologies, Inc. (FST) has been in the forefront of development of fiberoptic based invasive pressure sensing devices. Such devices are described in a number of U.S. Patents previously issued to FST, including U.S. Pat. Nos. 4,711,246 and 4,924,870 and pending U S. patent application Ser. No. 748,082, filed on Aug. 21, 1991, which are hereby incorporated by reference. Briefly, the systems described in the above referenced documents employ a catheter having a deformable diaphragm positioned near the distal end of an optical fiber. Deformation of the diaphragm in response to fluid pressure applied to its outside surface by the blood changes its shape and proximity to the end of the optical fiber. A light signal injected into the proximal end of the optical fiber exits the distal end of the fiber and is reflected to return along the fiber by the deformable diaphragm. The shape and spacing of the diaphragm from the fiber end affects the intensity of returned light which is calibrated to provide a pressure measurement.

Fiberoptic pressure sensor of the type described in FST's previously issued patents and pending application posses a number of fundamental advantages over the previously used approach of invasive blood pressure measurement which comprises the use of a catheter lumen communicating with a remote site within the body which is connected to an external fluid column type pressure measuring device. These systems posses inherent disadvantages that arise from mechanically coupling a blood pressure wave through a fluid column embedded within a catheter, to an external transducer. Both the mechanical compliance and the damping losses of the fluid column, the catheter material, and the transducer membrane result in broad resonance artifacts, typically occurring at frequencies in the vicinity of 10 to 20 Hertz, and limit high frequency response. Moreover, any extensions of the catheter link used, for example, for a bed ridden patient, often result in impedance mismatching between tubing and connectors which can create additional resonance peaks. Since significant blood pressure wave spectral components lie near the resonance frequencies of column sensors, some frequencies will be amplified relative to others, producing a distorted waveform. Waveform distortion is also produced by bubbles trapped in the fluid column. In addition, these types of pressure sensors suffer the disadvantage that distortions are caused by patient or catheter movement. Motion produces a shift in fluid column position which adds baseline or low frequency artifacts to the pressure waveform. It is for these reasons that direct pressure sensing at the tip of a catheter is becoming a preferred approach in clinical settings for pressure measurement and is gaining wider acceptance in such applications.

In addition to blood pressure monitoring, clinicians are often interested in evaluating other blood parameters. Most significant in many patient care settings is the monitoring of blood oxygen saturation which is defined as the fraction of oxygen bound to all available hemoglobin as compared to total oxygen binding capacity. Various approaches toward blood oxygen saturation evaluation are presently available. One type of clinical laboratory measuring device requires that blood samples be withdrawn from the body, and then transferred into the device. Such devices typically employ gas chromatography or use other methods such as optical spectroscopy. In the latter approach, a blood absorption spectrum is obtained over a continuous range of optical wavelengths. The extinction coefficients at the various wavelength can be used to determine the concentration of various blood species of clinical interest. Although continuous spectrum measurement produces the greatest amount of information, its unsuitability for use in clinical settings for real time analysis limits it applicability. Moreover, the cost of light sources and associated electronics required for such analysis are of concern.

As a compromise compared to continuous spectrum evaluation, there are presently available a number of fiberoptic based oxygen saturation sensors which are based on evaluating absorption extinction coefficients at a number of discrete wavelengths; for example, three wavelengths. The absorption extinction coefficients at these wavelengths are used to determine the concentration of oxyhemoglobin, which is the state of hemoglobin bound with oxygen. Absorption extinction coefficients are highly affected by hematocrit (the concentration of erythrocytes in the blood). Therefore, another wavelength source is used to measure hematocrit which is considered in deriving an oxygen saturation value. Although such devices using a limited number of discrete wavelengths are not capable of resolving many significant blood component species, they do provide clinically useful information.

Despite the existence of technology concerning fiberoptic pressure sensing and fiberoptic oxygen saturation measurement, such systems have heretofore not been combined in a single commercially viable sensor. The prior art teachings do, however, disclose the use of a fiberoptic based oxygen saturation measuring system employed in a catheter which also provides a lumen for fluid column pressure measurement. However, such a sensor posses the disadvantages previously discussed related to fluid column type pressure measurement. In addition to those shortcomings, such a combined sensor according to the prior art does not provide the ability to synchronize the measurement of oxygen saturation with the pressure reading. Other systems according to the prior art attempt to provide pressure measurement along with other measurements, such as blood gases or oxygen saturation using optical fibers. However, these systems have disadvantages of cost, reliability and limited accuracy. Simultaneous accurate measurement at the tip of a catheter of both oxygen saturation and pressure would offer unique physiological information not available today with existing instrumentation. In view of these factors, there is a current need in medicine to provide a sensing system providing such simultaneous measurement.

Presently available invasive fiberoptic oxygen saturation sensors are often subject to erroneous readings when the sensing tip is positioned o abut the walls of a blood vessel. To avoid misinterpreting readings taken in this condition, special data reduction algorithms must be applied or special procedures must be followed, complicating measurement. Even when the catheter is correctly placed, some catheters are affected by the movement of blood vessels, especially arteries in response to the blood pressure wave. It is therefore desirable to provide a sensor which is inherently not subject to such vessel wall effects.

In the design of catheter type sensing system for blood vessel access, a number of design considerations must be addressed. Most significantly, the catheter must have a small diameter so as to permit access to small caliper blood vessels and further to prevent occlusion of blood flow through the vessel where measurements are being taken. Cost of the catheter of the system is another important consideration, particularly where catheters are designed for single use application to prevent the spread of infection between patients or to medical personnel. Also significant is the cost associated with the sensing head of the sensor to which the catheter is connected which is designed for long term use. In that regard, is preferable to reduce the number of individual light sources and photodetectors used in the sensing head to inject light signals into the catheter and receive reflected back signals. An underlying consideration of paramount significance is the accuracy and reliability of the sensors which must be assured in that the devices are employed in critical patient care settings.

This invention relates to a novel fiberoptic sensor for simultaneous measurement of blood pressure and oxygen saturation. The sensor of this invention uses optical fibers exclusively for measurement. The sensor of this invention further provides an efficient and cost effective measuring system through the use of light sources which provide outputs which are shared between the pressure and oxygen saturation measuring fibers. By reducing the number of light emitters, the stability of optical signals is enhanced and a smaller sized and less complex sensing head is possible as compared with systems utilizing a greater number of independent elements.

The sensor of this invention also permits synchronizing outputs of the oxygen saturation fiber with that of the pressure measuring fiber, or visa versa. Such synchronous detection may be used to enhance measurement accuracy to provide additional information of clinical use. This invention further encompasses a sensor for oxygen saturation measurement based on the evanescent effect, which is believed to be relatively insensitive to hematocrit. And finally, this invention relates to sensors having sensing tips which are designed to inherently reduce the susceptibility to vessel wall effects.

Additional benefits and advantages of the present invention will become apparent to those skilled in the art to which this invention relates from the subsequent description of the preferred embodiments and the appended claims, taken in conjunction with the accompanying drawings.

BRIEF DESCRIPTION OF THE DRAWINGS

FIG. 5 is a cross-sectional view through a sensing tip in accordance with an embodiment of this invention employing a chamber for blood light absorption having a planar light reflective surface.

FIG. 6 is a partial cross-sectional view through a sensing tip similar to that shown in FIG. 5 but shown having a concave reflective surface.

DETAILED DESCRIPTION OF THE INVENTION

Figure 1:
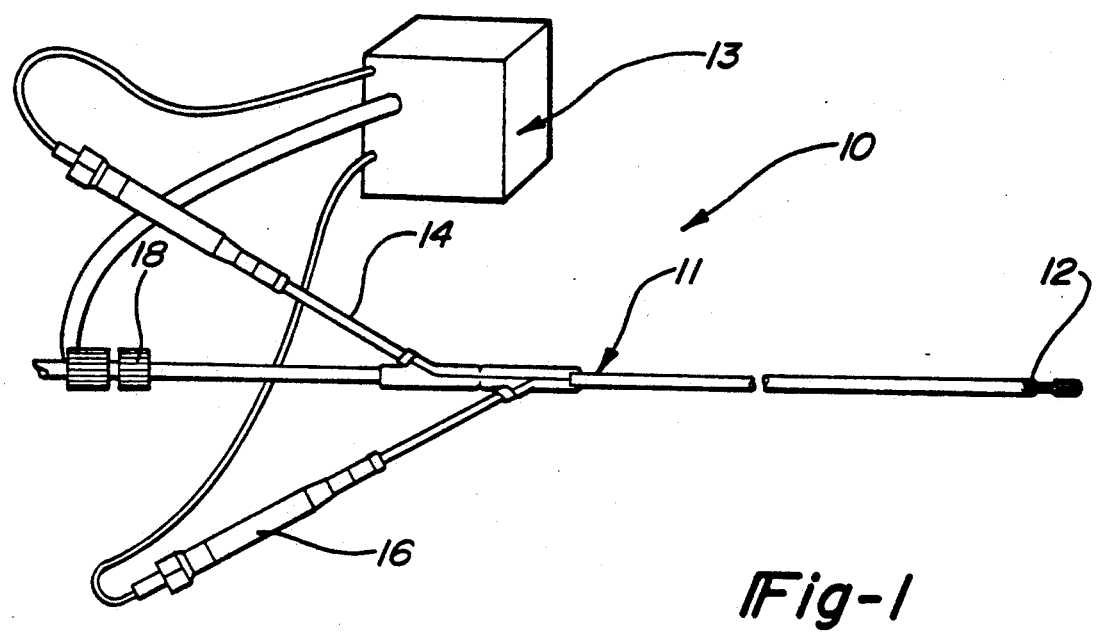
FIG. 1 is pictorial view of the sensor in accordance with this invention.

A sensor in accordance with this invention is shown in pictorial fashion in FIG. 1 and is designated there by reference number 10. Sensor 10 generally comprises catheter assembly 11 and sensor head 13. Catheter assembly 11 is adapted for introduction into human patient blood vessels. Catheter assembly 11 includes a sensing tip 12 which will be described in detail later in this description. Catheter assembly 11 includes fiber optic couplers 14 and 16 which are provided for connection to optical fiber within the catheter for pressure and oxygen saturation measurement. A lumen is provided with connector 18 for enabling a known fluid pressure to be applied at sensing tip 12 for purposes of calibrating the pressure sensing features of the sensor.

An optical fiber coupler 18 is provided as a termination for the optical fibers within the catheter which are provided for the transmission of light signals for both pressure and oxygenation sensing, as is described in more detail below. The catheter assembly incorporates a catheter outer covering or sheath 20 made of a material which reduces thrombolytic (clot forming) activity and would be made, for example, of a polymer which binds to heparin.

Figure 2:
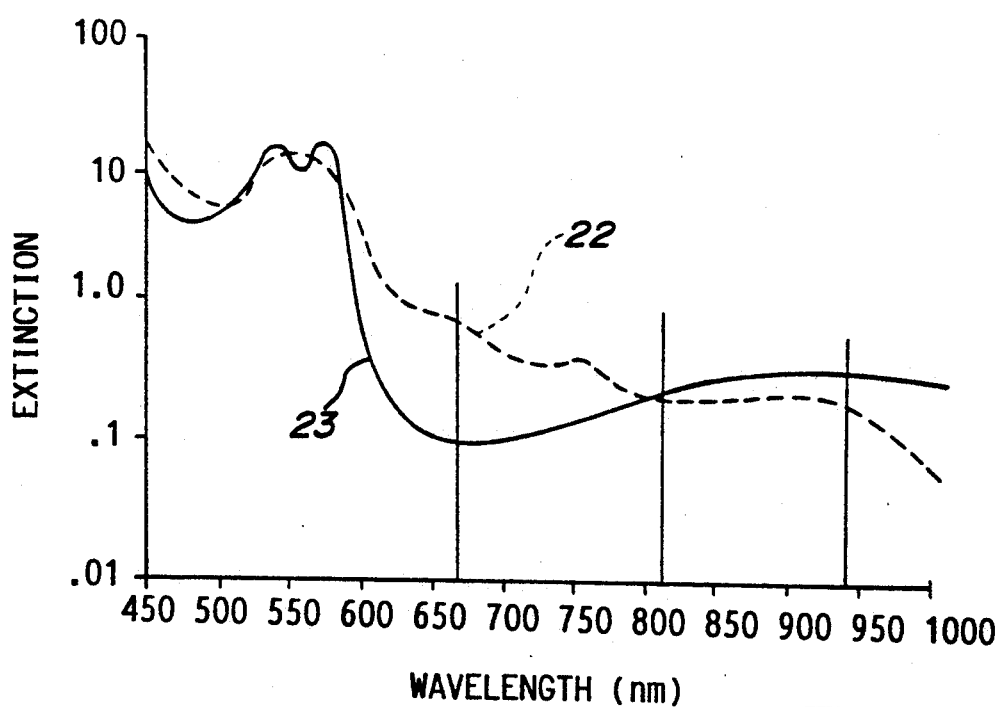
FIG. 2 is a optical spectrum showing absorption extinction coefficients for reduced hemoglobin and oxyhemoglobin.

Now with reference to FIG. 2, the general approach of providing oxygen saturation measurement provided by sensor 10 will be described. FIG. 2 provides a spectrum showing the extinction coefficients for absorption of reduced hemoglobin shown as curve 22, and oxyhemoglobin shown as curve 23 at various light wavelengths. At around 800 nm, the two spectrum curves overlap or define a "crossover point". Therefore, the extinction coefficients at that wavelength are the same for both reduced hemoglobin and oxy-hemoglobin. This characteristic is significant in that the extinction coefficient of light signals at that wavelength can be used as a measure of other parameters, for example hematocrit. For many sensor designs, and especially those relying on light absorption, hematocrit will strongly influence the extinction coefficient. Accordingly, by using a wavelength of around 800 nm, absorption of that signal can be used to calibrate the system for changes in hematocrit. It is also significant to note that at wavelengths below the crossover point, oxy-hemoglobin absorbs more than reduced hemoglobin, and the opposite occurs at wavelength above the crossover point. FIG. 2 designates several additional discrete wavelengths, namely, 660 nm and 940 nm which are employed for oxygen sensing systems in accordance with this invention.

Figure 3:
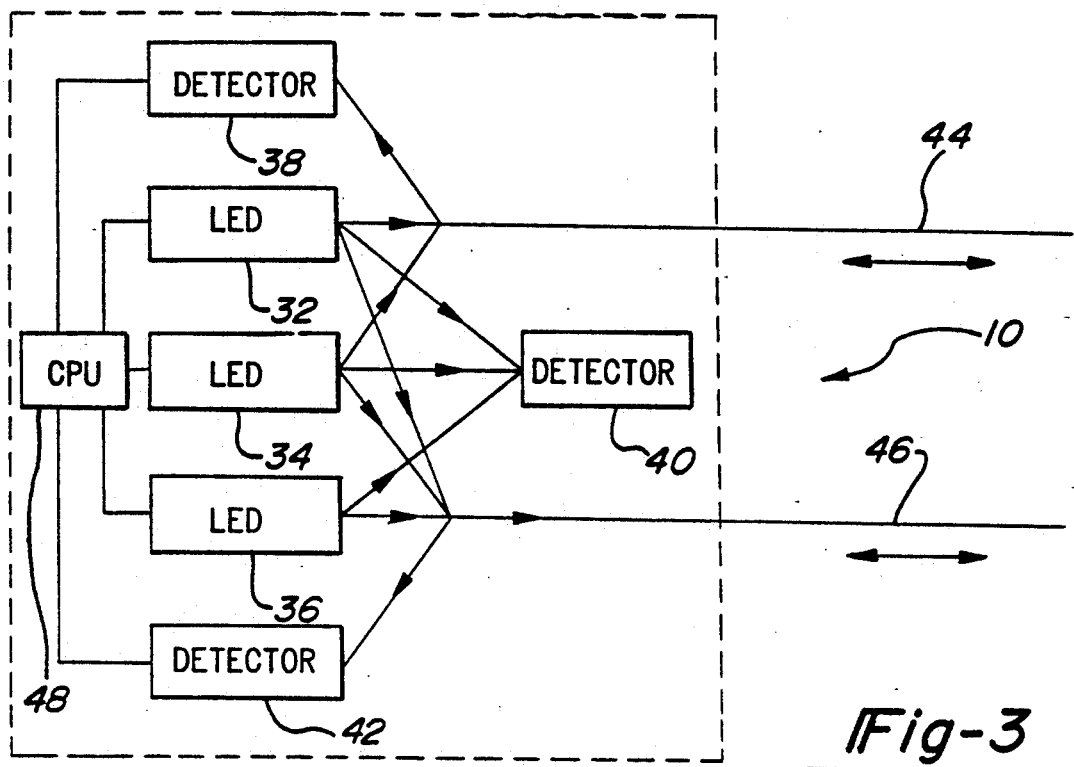
FIG. 3 is a schematic diagram of a sensor according to a first embodiment of this invention showing components of the sensing head and used with an oxygen sensing system incorporating a single optical fiber.

FIG. 3 illustrates in pictorial fashion a configuration for a sensor system 10 in accordance with this invention. The sensing head 13 is shown incorporating three discrete light sources, preferably in the form of LEDs or semiconductor lasers designated by references numbers 32, 34, and 36. Sensing head 13 also includes three photodetectors designated by reference numbers 38, 40 and 42. The lines connecting the various elements in FIG. 3 with direction arrowheads represent light paths which may be provided by sections of optical fibers. A single optical fiber 44 is provided for pressure sensing. The approach incorporated in sensor system 10 for pressure detection is identical to FST's sensing systems as described in the prior referenced patents in which a deformable diaphragm is employed to modulate the intensity of a returned light signal along fiber 44. Sensor system 10 also preferably incorporates a dual wavelength referencing system as described in FST's previously issued U.S. Pat. No. 4,924,870. That patent describes a system in which a reflective coating is deposited on the end of optical fiber 44 which reflects light below a threshold cutoff wavelength, while transmitting light having a greater wavelength. The intensity of the two returned back light signals are ratioed as a means of reducing sensitivity of the pressure sensing system to differences in fiber characteristics, and the effects of fiber bending and other signal noise.

In the system shown in FIG. 3, LED 32 is selected to emit light at a wavelength of about 810 nm which is inputted into optical fiber 44 and is fully reflected at the dielectric filter (not shown) at the end of the fiber and thus provides a reference or calibration signal. LED 34 emits light at a wavelength of 940 nm which is transmitted through the dielectric filter and is modulated by the deformable diaphragm. Light which is returned along optical fiber 44 is coupled to photodetector 38. Through the network of fiber connections shown in FIG. 3, photodetector 38 receives signals reflected back along optical fiber 44 relating both to the calibration signal emitted by LED 32 and the pressure measuring signal emitted by LED 34.

Sensor system 10 shown in FIG. 3 further incorporates a second optical fiber 46 which is provided for oxygen saturation measurement. All three LED's 32, 34, and 36 are coupled into optical fiber 46. LED 36 emits light at about 660 nm. Accordingly, light signals having wavelengths of 660, 810 and 940 nm are sent along optical fiber 46. With reference to FIG. 2, it can be seen that these wavelengths include the crossover point of the curves 22 and 23, and wavelengths above and below the crossover point. Light returned along optical fiber 46 is received by photodetector 42. Since the absorption relationship between oxygenated and reduced hemoglobin reverses at the crossover point, evaluating the absorption of light at the wavelengths of 660 and 940 nm provides a so called "push/pull effect" in which ratioing of those returned signals increases sensitivity.

In sensing head 13, reference photodetector 40 is coupled to each of LED's 32, 34, and 36 and is provided for the purposes of evaluating the output intensity of each of the LED's. Photodetector 40 is used in calibrating the returned back signals so that the system can comprehend changes in output which are attributable to the specific characteristics of an individual LED or changes which occur during its operating life span, or in response to temperature changes, driving current, etc. The optical fiber pathways shown in FIG. 3 can be provided through various branching techniques known in the optical fiber art. For example, an optical fiber can be initially formed from plural strands which are fused at a point along their length to one end, thus providing a branching fiber. In addition, so called "mixing balls" or other known fiber coupling techniques could be used.

In a preferred mode of operation of the system shown in FIG. 3, the sensing head 13 would incorporate a timing mechanism designated as CPU 48 for sequentially firing LED's 32, 34, and 36. Readings from photodetectors 38 and 42 would be synchronized so that the returned back signals at the various wavelengths can be discriminated. This synchronous demodulation technique avoids the requirement of providing wavelength selective optical filters as a means of discriminating the signals returned along fibers 44 and 46 at the various wavelengths.

The ability to provide simultaneous measurement of oxygen saturation and blood pressure at the sensing tip 12 of the sensor is believed to provide a number of significant attributes. For example, it is known that the orientation of red blood cells tends to change in response to the pressure difference between diastolic and systolic blood pressures. These orientation changes are known to change the light scattering effect of the blood. In particular, it is known that red blood cells tend to become oriented in a stacked-together fashion at the high pressure point of the pressure wave and become more randomly oriented in the lower pressure regions. Since oxygen saturation measurements, relying upon traditional absorption extinction coefficient measurement, are sensitive to scattering, such devices are subject to inaccuracy if they are sensitive to the pressure dependent effects of scattering which occur during a single blood pressure wave. In addition to scattering changes, blood vessel walls, especially arteries, tend to move or pulse in response to the pressure wave. This characteristic also can produce light attenuation changes as the wall moves relative to the sensor.

The simultaneous pressure and oxygen saturation measurement achievable by this invention would allow oxygen saturation measurements to be taken at a segment of the period of the pulse waveform such that light scattering tendencies of the blood will tend to be the same from one pulse to the next. In addition, observing absorption changes in measuring oxygen saturation in response to the pressure wave may also enable hematocrit to be evaluated without reference to a crossover wavelength, thus enabling a reduction in wavelengths used or enabling other blood species to be evaluated using a given number of available wavelengths.

Figure 4:
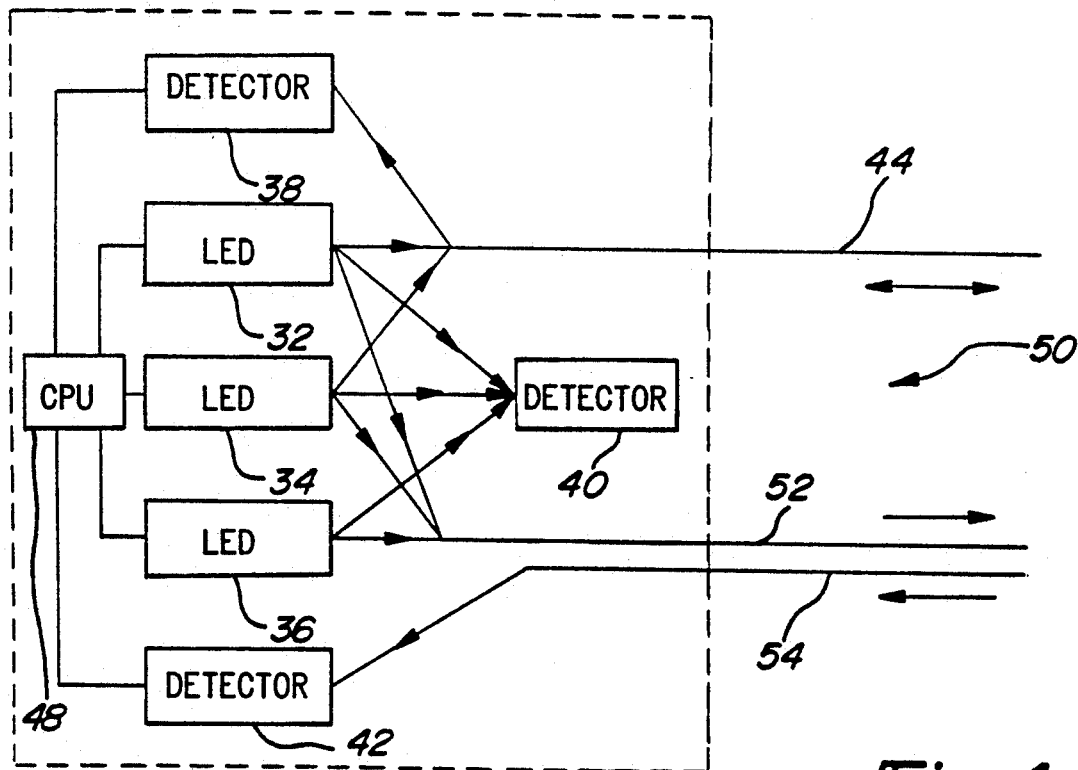
FIG. 4 is a schematic diagram of a sensor according to an alternate embodiment of this invention shown with the oxygen sensing system incorporating two optical fibers.

FIG. 4 is a pictorial view of a sensor system 50 in accordance with this invention which has many elements common with the prior embodiment but differs from that shown in FIG. 3 in that the oxygen saturation detection employs two separate fibers 52 and 54. Fiber 52 is used to conduct light signals to sensing tip 12, whereas a separate fiber 54 is provided only for the returned signal. This configuration may be advantageous in some applications since it would be possible to custom tailor fibers 52 and 54 in consideration of their roles. For example, the diameter of optical fiber 54 could be greater than that of fiber 52 for the purposes of increasing light gathering capability. It is also significant to note that optical fiber 54, shown in FIG. 4, is directly connected to photodetector 42 and does not have to be branched which results in a reduction in signal strength.

Now with reference to FIGS. 5 through 8, various alternative designs for sensing tip 12 are shown. As shown in FIG. 5, sensing tip 12 is connected to catheter sheath 20 through an interfitting connector, or alternately bonding or other joining techniques could be used. Pressure sensing optical fiber 44 terminates adjacent to deformable diaphragm 58. The pressure sensing features of sensing tip 12 are fully described in applicant's issued U.S. Patents mentioned previously. One difference, however, of tip 12 with respect to previous designs of applicant is the provision of a protective cap 60 terminating the sensing tip having pressure sensing openings 62. Cap 60 is provided to protect pressure diaphragm 58, especially from loading effects caused by contact with structures in the body. Cap 60 also aids in minimizing the sinitic effect of blood flow striking the diaphragm.

The oxygen sensing features of sensing tip 12 comprise a notched or recessed area within the side of tip. Sensing tip 12 incorporates a dual fiber oxygen saturation measuring approach as described in connection with FIG. 4. Spaced from the terminations of both fibers 52 and 54 is a mirror 66. Light emitted from fiber 52 passes through blood in the area of recess 64. The reflective surface of mirror 66 returns some of this signal in the direction of return fiber 54 which is transmitted to photodetector 42. As described previously, the absorption extinction coefficient associated with the transmission of light through the blood in the area of recess 64 is used as a means for measuring oxygen saturation. Since hematocrit affects the scattering of light passing through the area of recess 64, an independent measure of hematocrit is provided through transmission of light at the wavelength of 810 nm as explained previously. Apertures for the transmission of blood such as heparin or the withdrawal of fluid can be provided within sensing tip 12 or within catheter sheath 20 at a location near the sensing tip. By providing recess 64 having a depth (as measured from the outer surface of sheath 20 toward its longitudinal center axis) of at least two millimeters, it is believed possible to substantially reduce or eliminate the tendency for erroneous readings to be created when a blood vessel wall interferes with the transmission of light in the area of recess 64.

FIG. 6 illustrates a sensing tip 67 according to an alternate embodiment of the invention. The device is identical to sensing tip 12 described above except that reflective surface 68 is concave. This configuration increases the returned light signal strength. In all other respects, sensing tip 67 operates like tip 12.

Figure 7:
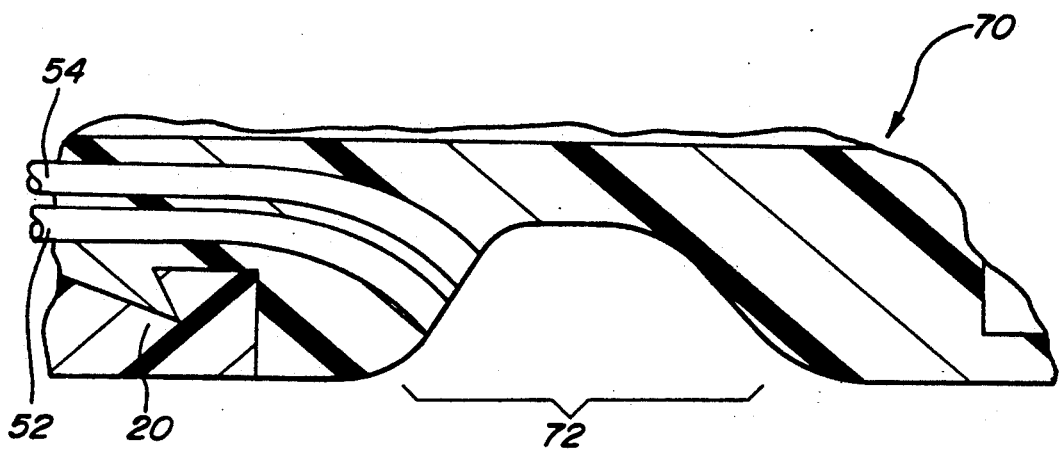
FIG. 7 is a partial cross-sectional view through a sensing tip according to an alternate embodiment of this invention based on back scatter measurement.

FIG. 7 illustrates a portion of sensing tip 70 in accordance with a alternate embodiment of this invention. Since sensing tip 70 incorporates many of the elements of sensing tip 12, these elements are identified by like reference numbers. Sensing tip 70 provides oxygen saturation measurement through the effect of evaluating back scatter radiation. In this case, light is emitted through fiber 52 in a field area provided by recess 72. Back scatter radiation is received by return optical fiber 54. Extinction coefficient curves similar to that attributable to absorption, shown in FIG. 2, also exist for the back scatter operational mode. As in the prior embodiments, recess 72 prevents blood vessel walls from directly confronting the fibers, thus reducing the likelihood of affecting oxygen saturation measurement.

Figure 8:
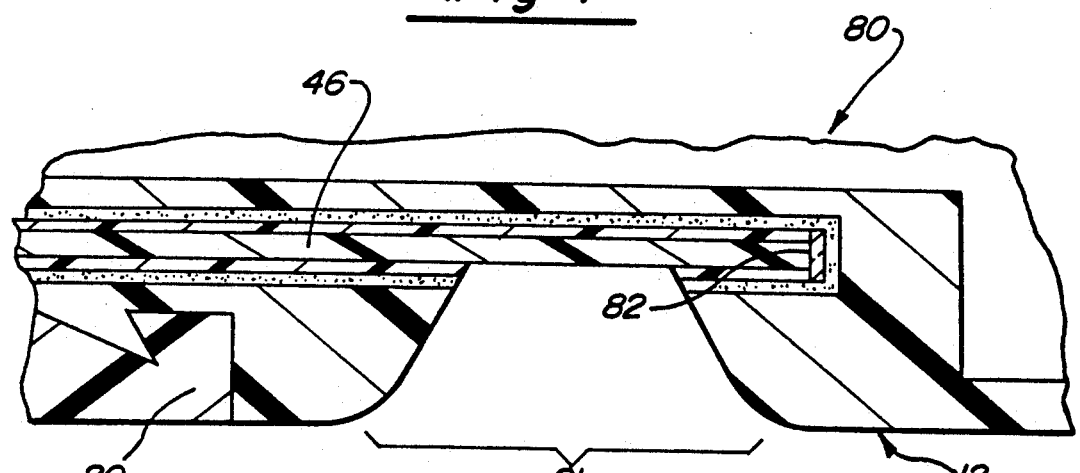
FIG. 8 is a partial cross-sectional view through a sensing tip according to an embodiment of this invention based on an evanescence measurement.
Figure 9:
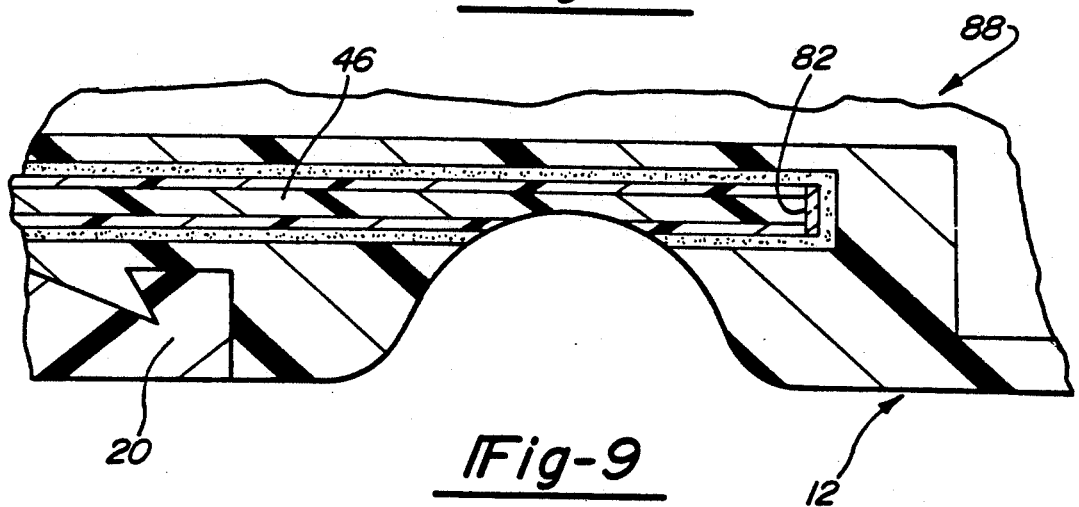
FIG. 9 is a partial cross-sectional view through a sensing tip according to an alternate embodiment of this invention based on a modified evanescence measurement in which the optical fiber cross section is perturbed.

A second class of sensing tip designs according to this invention are shown in FIGS. 8 and 9, and employ an evanescent principle for examining the interaction of light of known wavelengths with erythrocytes. In employing the evanescent effect, light is propagated along an optical fiber which has a polished outer surface region 81 exposed to blood. Since blood contains erythrocytes which absorb light of various wavelengths in a characteristic fashion, a fraction of the energy transmitted along the fiber tends to leak from the fiber into the absorber. The fraction of the light of a given wavelength which leaves the fiber is related to the absorption characteristics of the blood. The principal advantage of employing the evanescence phenomenon is that it is not subject to scattering error since it does not rely on light propagating through blood. Therefore, it is possible that a sensor relying on evanescence may not require a third discrete wavelength or other signal reduction for the purpose of calibrating for scattering differences due to hematocrit.

In FIG. 8, sensing tip 80 is shown employing a single optical fiber 46 for oxygen saturation measurement. The terminal end of the fiber 46 is coated with a reflective film 82. Within recess 84, the original fiber thickness is reduced by slightly polishing away a few microns to facilitate strong interaction between the evanescent field and blood cells. The sensitivity of the sensor can be increased through increasing the length of region 81 and recess 84.

In FIG. 9, sensing tip 88, like that of FIG. 8, employs a single fiber 46 for oxygen saturation measurement terminated by reflective film 82. Sensing tip 88, however, employs a modified evanescent transmission coupling effect where a geometry perturbation is applied to the fiber core. A local thinning or tapering of the core enhances sensitivity to oxygen concentration changes. The core is perturbed as shown in FIG. 9 by milling away a portion of its diameter. Other core perturbations could be provided, such as removing wedge shaped slices or generating special surface roughness features. The essence of sensing tip 88 is a local change in the cross-sectional shape of the fiber core along its length.

While the above description constitutes the preferred embodiments of the present invention, it will be appreciated that the invention is susceptible of modification, variation and change without departing from the proper scope and fair meaning of the accompanying claims.

We claim:

1. A sensor for in vivo evaluation of blood pressure and blood oxygen saturation of a patient, comprising:
a catheter having a distal end for introduction within patient blood vessels and a proximal end, said catheter having at least a first optical fiber means for blood pressure sensing and a second optical fiber means separate from said first optical fiber means for blood oxygen saturation measurement,
a sensing tip affixed to said catheter distal end having pressure sensing means for modulating a light signal sent along said first optical fiber means, said sensing tip further having means for causing said blood to interact with a light signal sent along said second optical fiber means, said means for causing having a chamber which is filled with blood when said sensing tip is within said blood vessels and is positioned adjacent the distal end of said second optical fiber means, said chamber defining a concave reflective surface means for reflecting light signals emitting from said second optical fiber means after passing through said blood back into said second optical fiber means, and a sensing head means coupled to said catheter proximal end for injecting light signals into said first and second optical fiber means and for receiving light signals returned along said first and second optical fiber means thereby enabling said blood pressure and blood oxygen saturation evaluation, said sensing head having at least a first light source coupled into said first and second optical fiber means.

2. A sensor according to claim 1 wherein said pressure sensing means comprises a deformable diaphragm positioned adjacent the distal end of said first optical fiber means and adapted to be exposed to said blood whereby said diaphragm is deformed in response to blood pressure, and said diaphragm modulating the intensity of a light signal sent along said first optical fiber means.

3. A sensor according to claim 1 wherein said catheter further comprises a lumen means for calibrating said pressure sensing means by allowing a known pressure of a fluid to act on said pressure sensing means.

4. A sensor according to claim 1 wherein said means for causing defines a recess adjacent said distal end and including a termination of said second optical fiber means which is displaced at least 2 millimeters from the outer surface of said catheter toward a longitudinal center axis of said catheter tip.

5. A sensor according to claim 1 wherein said second optical fiber means comprises a single optical fiber for transmitting both an inputted and returned light signals.

6. A sensor according to claim 1 wherein said second optical fiber means comprises a pair of optical fibers with a first fiber for transmitting an inputted light signal and a second fiber for transmitting a returned light signal.

7. A sensor according to claim 1 wherein said first optical fiber means comprises a reflective surface at the distal end of said first optical fiber means for reflecting light from said first light source to form a reference signal for blood pressure measurement.

8. A sensor assembly according to claim 7 wherein at least one of said first and said second fiber means comprise a fiber core having a main section within said catheter and a branching portion within said sensing head means optically coupled to said first light source.

9. A sensor according to claim 1 wherein said sensing head means comprises a second light source coupled to both said first and second optical fiber means.

10. A sensor according to claim 9 wherein both said first and second fiber means comprise a fiber core having a main section within said catheter and separate branching portions within said sensing head means optically coupled to said first and second light sources.

11. A sensor according to claim 1 wherein said sensing head means measures a blood pressure waveform from said light signals and said sensing head means gates light signals received along said second fiber means in response to said waveform to evaluate blood oxygen concentration during a prescribed segment of a period of said waveform.

12. A sensor for in vivo evaluation of blood pressure and blood oxygen saturation of a patient, comprising:
a catheter having a distal end for introduction within patient blood vessels and a proximal end, said catheter having a sensing tip having a means for sensing blood pressure and a means for sensing blood oxygen, said blood pressure sensing means enabling a blood pressure waveform responsive to a heartbeat to be measured, and a sensing head means coupled to said proximal end of said catheter for gating signals received from said blood oxygen sensing means in response to said waveform to evaluate blood oxygen concentration during a prescribed segment of a period of said waveform thereby minimizing pressure dependent effects on blood oxygen saturation by said blood oxygen sensing means.

13. A sensor according to claim 12 wherein said pressure sensing means comprises a deformable diaphragm positioned adjacent the distal end of a first optical fiber means extending between said catheter distal and proximal ends and adapted to be exposed to said blood whereby said diaphragm is deformed in response to blood pressure, and said diaphragm modulating the intensity of a light signal sent along said first optical fiber means.

14. A sensor according to claim 13 wherein said blood oxygen sensing means comprising a second optical fiber means for causing light inputted into said second optical fiber means to be modulated in response to blood oxygen content.

15. A sensor for in vivo evaluation of blood pressure and blood oxygen saturation of a patient, comprising:
a catheter having a distal end for introduction within patient blood vessels and a proximal end, said catheter having at least a first optical fiber means for blood pressure sensing and a second optical fiber means separate from said first optical fiber means for blood oxygen saturation measurement, a sensing tip affixed to said catheter distal end having pressure sensing means for modulating a light signal sent along said first optical fiber means, said sensing tip further having means for causing said blood to interact with a light signal sent along said second optical fiber means including a surface along a section of a fiber of said second optical fiber means adapted to be exposed to said blood wherein light traveling along said fiber interacts with said blood through an evanescence effect and a reflective surface is positioned at the terminal end of said second optical fiber means whereby light signals cross past said fiber section and are thereafter reflected back along said second optical fiber means, and a sensing head coupled to said catheter proximal end for injecting light signals into said first and second optical fiber means and for receiving light signals returned along said first and second optical fiber means thereby enabling said blood pressure and blood oxygen saturation evaluation, said sensing head having at least a first light source coupled into said first and second optical fiber means.

16. A sensor according to claim 15 wherein said second of said fiber comprises a polished length of the outer surface of said fiber adapted to be in direct contact with said blood.

17. A sensor for in vivo evaluation of blood pressure and blood oxygen saturation of a patient, comprising:
a catheter having a distal end for introduction within patient blood vessels and a proximal end, said catheter having at least a first optical fiber means for blood pressure sensing and a second optical fiber means separate from said first optical fiber means for blood oxygen saturation measurement,
a sensing tip affixed to said catheter distal end having pressure sensing means for modulating a light signal sent along said first optical fiber means, said sensing tip further having means for causing said blood to interact with a light signal sent along said second optical fiber means in the form of a polished length of the outer surface of fiber of said second optical fiber means adapted to be in direct contact with said blood along a section of said fiber of said second optical fiber means adapted to be exposed to said blood wherein light traveling along said fiber interacts with said blood through an evanescence effect, and
a sensing head coupled to said catheter proximal end for injecting light signals into said first and second optical fiber means and for receiving light signals returned along said first and second optical fiber means thereby enabling said blood pressure and blood oxygen saturation evaluation, said sensing head having at least a first light source coupled into said first and second optical fiber means.

18. A sensor for in vivo evaluation of blood pressure and blood oxygen saturation of a patient, comprising:
a catheter having a distal end for introduction within patient blood vessels and a proximal end, said catheter having at least a first optical fiber means for blood pressure sensing and a second optical fiber means separate from said first optical fiber means for blood oxygen saturation measurement,
a sensing tip affixed to said catheter distal end having pressure sensing means for modulating a light signal sent along said first optical fiber means, said sensing tip further having means for causing said blood to interact with a light signal sent along said second optical fiber means in a form of a surface along a section of a fiber of said second optical fiber means having a perturbation of the cross-sectional configuration of said fiber along said surface, said surface adapted to be exposed to said blood wherein light traveling along said fiber interacts with blood through an evanescence effect, and
a sensing head coupled to said catheter proximal end for injecting light signals into said first and second optical fiber means and for receiving light signals returned along said first and second optical fiber means thereby enabling said blood pressure and blood oxygen saturation evaluation, said sensing head having at least a first light source coupled into said first and second optical fiber means.

19. A sensor according to claim 18 wherein said perturbation comprises a local reduction in the cross sectional area of said fiber.

* * * * *

UNITED STATES PATENT AND TRADEMARK OFFICE
CERTIFICATE OF CORRECTION

PATENT NO. : 5,280,786
DATED : January 25, 1994
INVENTOR(S) : Marek T. Wlodarczyk, Charles D. Anderson, Daniel L. Vokovich It is certified that error appears in the above-indentified patent and that said Letters Patent is hereby corrected as shown below:

Column 9, line 66, Claim 11, after "signals" insert --returned along said first optical fiber means--.

Column 11, line 16, Claim 17, after "of" insert --a--.

Signed and Sealed this

Seventeenth Day of January, 1995

Attest:

BRUCE LEHMAN

Attesting Officer

Commissioner of Patents and Trademarks